United States Patent [19]

Riceberg

[11] 4,399,228

[45] Aug. 16, 1983

[54] POLATE COMPETITIVE PROTEIN BINDING ASSAY

[75] Inventor: Louis J. Riceberg, Needham, Mass.

[73] Assignee: Corning Glass Works, Corning, N.Y.

[21] Appl. No.: 288,477

[22] Filed: Jul. 30, 1981

[51] Int. Cl.³ ..................... G01N 33/54; G01N 33/56; G01N 33/58

[52] U.S. Cl. ..................................... 436/505; 422/61; 436/804; 436/808; 436/542

[58] Field of Search ............... 436/505, 542, 804, 808; 424/1

[56] References Cited

U.S. PATENT DOCUMENTS

| | | | |
|---|---|---|---|
| 4,146,602 | 3/1979 | Gutcho et al. | 424/1 |
| 4,336,185 | 6/1982 | Niswender | 424/1 |
| 4,350,659 | 9/1982 | Riceberg | 424/1 |

OTHER PUBLICATIONS

Kamen et al., J. Lab. Clin. Med, 83:164–174 (1974).
Theobald et al., Clin. Chem. 27:553–555 (1981).

*Primary Examiner*—Christine M. Nucker
*Attorney, Agent, or Firm*—W. E. Maycock

[57] ABSTRACT

Improvement in a competitive protein binding assay for N-5-methyltetrahydrofolic acid wherein any folate standard used is N-5-methyltetrahydrofolic acid complexed with folate binder protein. The protein of the complex is destroyed prior to the addition of immobilized folate binder protein. The immobilized folate binder protein participates in competitive binding with unknown folate and labeled folate reagents.

11 Claims, No Drawings

POLATE COMPETITIVE PROTEIN BINDING ASSAY

BACKGROUND OF THE INVENTION

Folate deficiency is a common cause of megaloblastic anemia in man. In the human body, folic acid is metabolized to tetrahydrofolic acid and subsequently to N-5-methyltetrahydrofolic acid, which in turn can be reconverted to tetrahydrofolic acid in the presence of vitamin $B_{12}$ to reenter the metabolic pool of 1-carbon fragment donors and acceptors. It is important to be able to measure the amount of N-5-methyltetrahydrofolic acid in the serum, plasma and/or red blood cells.

Quite often, the concentration of N-5-methyltetrahydrofolic acid, the major folate derivative in blood, is measured using a competitive protein binding assay. As will be explained more fully hereinbelow, a competitive protein binding assay for N-5-methyltetrahydrofolic acid should preferably include the utilization of N-5-methyltetrahydrofolic acid in the standard reagents. However, N-5-methyltetrahydrofolic acid is very unstable, requiring measures such as sealing in ampoules in lyophilized form under a nitrogen atmosphere for proper storage. Such techniques are very impractical in the manufacture of an assay reagent kit. Furthermore, hermetic sealing could not prolong stability after reconstitution, which for N-5-methyltetrahydrofolic acid is only about three days at 4° C.

Because of the relationship between vitamin $B_{12}$ and folid acid in man, assays have been developed which are used to determine not only the N-5-methyltetrahydrofolic acid level, but also the concentration of vitamin $B_{12}$ using a single multi-step assay procedure. See the protocol of U.S. Pat. No. 4,146,602 for a purported description of a simultaneous vitamin $B_{12}$/folate radioassay. In fact, since vitamin $B_{12}$ and folate deficiencies are hematologically and clinically indistinguishable, it is usually necessary to determine the level of vitamin $B_{12}$ in the serum and the level of folate in the serum and red blood cells to help establish definitively the etiology of megaloblastic anemia.

Among various preservative compounds which can be employed to stabilize N-5-methyltetrahydrofolic acid, ascorbic acid is preferred. However, ascorbic acid is known to interfere with competitive binding vitamin $B_{12}$ analysis. Because of the known instability of N-5-methyltetrahydrofolic acid, many folate assays requiring folate standard(s), particularly using a simultaneous vitamin $B_{12}$/folate assay technique, have used the parent compound, folic acid, as the folate standard. However, folic acid does not always duplicate the activity of N-5-methyltetrahydrofolic acid in the testing procedure.

SUMMARY OF THE INVENTION

An object of this invention is to provide an improved competitive protein binding assay procedure employing a specific stabilized N-5-methyltetrahydrofolic acid reagent.

Still another object of this invention is to provide an improved competitive protein binding radioassay for simultaneously determining the levels of both N-5-methyltetrahydrofolic acid and vitamin $B_{12}$.

Another object of this invention is to provide a folate competitive protein binding assay characterized by improved accuracy in the determination of N-5-methyltetrahydrofolic acid levels.

Other objects of the present invention will be apparent to the skilled artisan from the detailed description of the invention hereinbelow.

In accordance with the present invention, the concentration of N-5-methyltetrahydrofolic acid in a patient sample is determined by separately admixing the patient sample and at least one standard reagent with known amounts of labeled folic acid or labeled folic acid derivative to yield at least two separate test samples, said at least one standard reagent comprising a reconstituted lyophilized complex of N-5-methyltetrahydrofolic acid-folate binding protein, destroying the folate binder protein of said at least one standard reagent and destroying any binding protein present in the patient sample, adding a known amount of folate binding protein, preferably immobilized on an inert support, to each test sample, and determining the amount of N-5-methyltetrahydrofolic acid in the patient sample by measuring the amount of labeled folic acid or labeled folic acid derivative which does or does not bind to the immobilized binder protein of each test sample and comparing the measurement obtained from the patient sample with the measurement(s) obtained from the at least one standard reagent.

Preferably, a plurality of known N-5-methyltetrahydrofolic acid reagents of differing concentration levels are run side-by-side with patient unknown samples for use in plotting a standard curve for use in determining by interpolation the concentration of N-5-methyltetrahydrofolic acid in the patient sample, as is fully known in the art.

In a preferred embodiment of the present invention, the N-5-methyltetrahydrofolic acid determination is carried out as part of a simultaneous vitamin $B_{12}$/folate assay.

In another preferred embodiment of the present invention, radioactive labels are used.

In still another preferred embodiment of the invention, the folate binder protein present in the standard reagent sample(s) and any endogenous binder protein present in the patient sample are destroyed by heating the test samples after addition of labeled folic acid or labeled folic acid derivative thereto at a temperature and for a time sufficient to destroy said proteins. Also, where desired, binders can be destroyed before addition of the labeled folic acid or labeled folic acid derivative to the system.

DETAILED DESCRIPTION OF THE INVENTION

As explained briefly hereinbefore, stability problems have hindered the use of N-5-methyltetrahydrofolic acid in competitive protein binding assays, particularly of the simultaneous vitamin $B_{12}$/folate type. The present invention provides an improved folate assay through the use of a stable complex of N-5-methyltetrahydrofolic acid with folate binding protein. This complex is described in detail in my copending application Ser. No. 288,463, now U.S. Pat. No. 4,350,659, incorporated herein by reference.

The binding protein, as far as known, can be any folate binding protein, for example, folate binding protein purified from bovine milk. The complex is formed by admixing unlabeled N-5-methyltetrahydrofolic acid with the binding protein in a liquid medium, allowing the complex to form using suitable conditions of incubation, followed by rapid freezing and dehydration of the mixture, preferably by lyophilization thereof, to form a dry powder.

For example, to an aqueous solution containing 20 ng/ml of N-5-methyltetrahydrofolic acid, there is added 66.4 micrograms of bovine folate binding protein. Thereafter, following incubation at 4° C. for two hours, lyophilization thereof is carried out. The lyophilized specimen can be reconstituted by the addition of water thereto as needed. This reconstituted material has increased stability compared to material without binding protein.

In addition to the folate binding protein obtained from bovine milk mentioned above, other commercially available as well as experimentally obtainable folate binding proteins such as goat milk folate protein binder, receptors or binders extracted from various animal organs, particularly kidneys, livers, and pancreas, β-lactoglobulin preparations or dolphin serum could be substituted therefor.

The folic acid or folic acid derivative can be labeled using any suitable labeling technique, such as by employment of a radioactive label, an enzyme label, a fluorescent label, and so forth. A radioactive label is preferred, such as radioactive iodine, i.e., $^{125}I$. Where the assay procedure is a simultaneous assay with determination of folate along with vitamin $B_{12}$, it is convenient to use different labels for the folic acid or folic acid derivative and the vitamin $B_{12}$ reagents.

The following example illustrates an embodiment of the present invention where a single patient sample is simultaneously analyzed for N-5-methyltetrahydrofolic acid concentration and vitamin $B_{12}$ concentration. However, such example is not to be construed as limiting the present invention in any manner. For example, incubation times, sample size, temperatures, and other factors can be varied, as is well-known in the art.

EXAMPLE

Reagents Used in the Assay

A. Binding Proteins

The binding proteins (folate binding protein, purified from bovine milk, and purified hog intrinsic factor as binding protein for vitamin $B_{12}$) are covalently bound to glass particles, which are suspended in 0.03 M pH 7.4 phosphate buffered saline (0.15 M in sodium chloride) containing 0.02% sodium azide as preservative.

B. Combined [$^{57}Co$] Vitamin $B_{12}$ and [$^{125}I$] Folate

[$^{57}Co$] Vitamin $B_{12}$ and [$^{125}I$] folate are dissolved in 0.1 M borate buffer pH 9.3 containing 0.001% potassium cyanide, amaranth red dye (2 micrograms per ml) as a pipetting aid and 0.2% sodium azide as preservative.

C. Dithiothreitol

One vial containing dithiothreitol is supplied in lyophilized form.

D. Vitamin $B_{12}$/Folate Standards

Six concentrations of vitamin $B_{12}$ and N-5-methyltetrahydrofolic acid in 0.1 M phosphate buffered saline pH 7.4 containing 1% human serum albumin and 0.2% sodium azide as preservative, having been lyophilized in the presence of a five-fold excess of folate binding protein.

E. Vitamin $B_{12}$/Folate Reference Controls

Two vitamin $B_{12}$/N-5-methyltetrahydrofolic acid reference controls are prepared from defibrinated human plasma and lyophilized in the presence of folate binding protein.

In the preparation of the above reagents D and E, N-5-methyltetrahydrofolic acid in the form of a complex with folate binding protein purified from bovine milk is used as the "folate" component.

The storage, handling and reconstitution conditions for the reagents are known to the skilled clinician. The dithiothreitol was reconstituted with reagent B at a level of 2 mg/ml to enhance nonspecific binding and improve stability of the N-5-methyltetrahydrofolic acid and vitamin $B_{12}$ during heating. The reference controls, which are optional, are selected in this embodiment to be at approximate concentration levels to yield assay results approximating folate deficient and normal patient ranges and vitamin $B_{12}$ normal and elevated ranges. These can serve as a check on the performance of the assay when handled in the same manner as the unknown sample.

In this particular example, the six vitamin $B_{12}$/folate standards are selected as set forth below, with the skilled artisan being able to modify their number, their concentrations, and the like in accordance with laboratory standards. The concentrations of the standards are per milliliter.

Contents of Tube (per ml)

Vitamin $B_{12}$/Folate Standard, 0/0 pg/ng
Vitamin $B_{12}$/Folate Standard, 100/1.0 pg/ng
Vitamin $B_{12}$/Folate Standard, 250/2.5 pg/ng
Vitamin $B_{12}$/Folate Standard, 500/5.0 pg/ng
Vitamin $B_{12}$/Folate Standard, 1000/10.0 pg/ng
Vitamin $B_{12}$/Folate Standard, 2000/20.0 pg/ng

Assay Procedure

Pyrex ® glass or polypropylene test tubes are used in duplicate for all runs, that is for running standards controls and for each patient sample.

In this particular assay embodiment, serum or plasma (EDTA anticoagulant added) can be used. Also, a whole blood lysate can be prepared and stabilized with ascorbic acid for carrying out a red blood cell folate analysis.

1. The test tubes are set up as follows:

| Tube Number | Contents of Tube (per ml) |
| --- | --- |
| 1, 2 | Vitamin $B_{12}$/Folate Background Standard, 0/0 pg/ng |
| 3, 4 | Vitamin $B_{12}$/Folate Standard, 100/1.0 pg/ng |
| 5, 6 | Vitamin $B_{12}$/Folate Standard, 250/2.5 pg/ng |
| 7, 8 | Vitamin $B_{12}$/Folate Standard, 500/5.0 pg/ng |
| 9, 10 | Vitamin $B_{12}$/Folate Standard, 1000/10.0 pg/ng |
| 11, 12 | Vitamin $B_{12}$/Folate Standard, 2000/20.0 pg/ng |
| 13, 14 | Vitamin $B_{12}$/Folate Control 1 |
| 15, 16 | Vitamin $B_{12}$/Folate Control 2 |
| 17, 18 | Patient serum sample (unknown) |

2. Add 100 µl of the appropriate standard, control or sample to the test tube.

3. Add 1.0 ml of reagent B (radioactive tracer vitamin B$_{12}$/folate) to each tube.

4. Mix well.

5. Incubate in boiling water for 15 minutes and then at room temperature for another 15 minutes.

This step destroys the folate protein binder used to form the N-5-methyltetrahydrofolic acid complex while at the same time destroys any endogenous folate binding protein in the biological sample.

6. Add 0.5 ml of reagent A (folate and vitamin B$_{12}$ binding proteins) to each tube.

7. Mix well.

8. Incubate for 1 hour at room temperature.

At least during the incubation steps, the tubes preferably are protected from light.

9. Centrifuge all tubes.

10. Decant all tubes.

11. Count all tubes with a gamma counter capable of counting $^{57}$Co and $^{125}$I simultaneously or separately.

In this example, the pellet is counted, but the decanted liquid could be counted as well, with modification of the calculations and generation of standard curves.

In addition, the binding protein reagent A could be immobilized on another support, such as an organic polymer, inorganic particles and so on. Although covalent bonding is preferred to link the binder protein to the support, with the bonding being directly to the support or through a spacer moiety as known in the art, other types of chemical and/or physical bonding techniques such as the use of ionic bonds, van der Waals forces and so on could be employed. In this assay, the binding protein is covalently bound to porous glass particles via silane coupling and glutaraldehyde as is well-known in the art (see, e.g., U.S. Pat. No. 3,669,841).

The determination of level(s) of unknown(s) in the patient sample can be accomplished using any of a number of data reduction calculation modes known to the skilled artisan. For example, relative percent bound for labeled vitamin B$_{12}$ and labeled folate for standard, controls and the unknown can be calculated using the following formula:

$$\text{Relative \% bound} = \frac{\text{mean cpm of sample}}{\text{cpm of 0/0 standard}} \times 100$$

Thereafter, standard curves can be generated by plotting on semilogarithmic (3 cycle) graph paper the relative percent bound on the linear axis and concentrations of the standards on the logarithmic axis. Interpolation yields vitamin B$_{12}$ and folate levels for unknowns and also for the controls as a check.

In a similar manner, folate concentration in the red blood cell lysate can be determined, as known to the skilled artisan.

As is well known in the art, the quantitative determination of the concentration of N-5-methyltetrahydrofolic acid in a sample requires the use of at least two standards having concentrations sufficiently different to define a standard curve. Such procedure was employed in the above example. It should be apparent to one having ordinary skill in the art, however, that a single standard can be employed if one needs only to determine whether or not the N-5-methyltetrahydrofolic acid concentration in the sample is above or below some given value.

Certain parameters known to the skilled artisan for use in the type of folate and/or vitamin B$_{12}$/folate assays as above described have not been discussed herein, for example that the assay would usually be carried out at a pH of around 9.2, and so on. Since the present invention through the use of immobilized binding protein and the N-5-methyltetrahydrofolic acid complex provides significant improvements over prior art folate and prior art folate/vitamin B$_{12}$ competitive protein binding assays, the parameters, conditions, reagents, etc. which would be used as disclosed in the prior art do not form part of the inventive feature herein and accordingly need not be described at all or described in great detail herein.

Variations of the invention will be apparent to the skilled artisan.

What is claimed is:

1. A process for determining the concentration of N-5-methyltetrahydrofolic acid in a biological sample of unknown N-5-methyltetrahydrofolic acid concentration which comprises separately admixing the biological sample and at least one standard reagent with known quantities of labeled folic acid or labeled folic acid derivative to yield at least two separate test samples, said at least one standard reagent comprising a reconstituted lyophilized complex of N-5-methyltetrahydrofolic acid-folate binding protein, destroying the folate binding protein of said at least one standard reagent and destroying any binding protein present in the biological sample, adding a known quantity of folate binding protein to each test sample, measuring the amount of labeled folic acid or labeled folic acid derivative which does or does not bind to the added binding protein in each test sample and from said measurements determining the concentration of N-5-methyltetrahydrofolic acid in the biological sample.

2. The process of claim 1 wherein the known quantity of folate binding protein added to each test sample is immobilized on an inert support.

3. A process comprising:
   (A) complexing N-5-methyltetrahydrofolic acid with folate binding protein in an aqueous based medium;
   (B) lyophilizing said aqueous based medium containing said complex; and
   (C) carrying out a competitive protein binding assay for N-5-methyltetrahydrofolic acid using the lyophilized complex in reconstituted form as a N-5-methyltetrahydrofolic acid reagent.

4. The process of any of claims 2 or 3 wherein the assay being carried out is a simultaneous vitamin B$_{12}$/folate assay.

5. The process of any of claims 2 or 3 wherein a plurality of reconstituted lyophilized N-5-methyltetrahydrofolic acid reagents, each having a different N-5-methyltetrahydrofolic acid concentration, wherein the N-5-methyltetrahydrofolic acid is complexed with folate binding protein, are run side-by-side along with the unknown sample and then the concentration of the folate in the unknown is determined by generating a standard curve from said known concentration reagents and comparing said unknown with said standard curve.

6. The process of claim 4 wherein a plurality of reconstituted lyophilized N-5-methyltetrahydrofolic acid reagents, each having a different N-5-methyltetrahydrofolic acid concentration, wherein the N-5-methyltetrahydrofolic acid is complexed with folate binding protein, are run side-by-side along with the unknown sample and then the concentration of the folate in the unknown is determined by generating a standard curve from said known concentration reagents and comparing said unknown with said standard curve.

7. The process of any of claims 2 or 3 wherein the label is radioactive.

8. The process of claim 4 wherein the label is radioactive and wherein a radioactive vitamin $B_{12}$ standard reagent is used in a competitive binding assay for vitamin $B_{12}$ and the radioactive label of said vitamin $B_{12}$ reagent is different than the radioactive label of said labeled folic acid or labeled folic acid derivative.

9. A competitive protein binding assay kit comprising:
    (A) N-5-methyltetrahydrofolic acid complexed with folate binding protein and
    (B) folate binding protein immobilized on an inert support.

10. The assay kit of claim 9 as a radioassay kit, said kit containing a plurality of standard lyophilized N-5-methyltetrahydrofolic acid reagents, each having upon reconstitution a different N-5-methyltetrahydrofolic acid concentration, wherein the N-5-methyltetrahydrofolic acid is complexed with folate binding protein, so that a standard folate binding curve can be generated from said standard reagents.

11. The radioassay kit of claim 10 wherein the inert support is silane-glutaraldehyde derivatized glass particles and the folate binding protein is covalently bound thereto.

* * * * *